US011375950B2

(12) United States Patent
Meirav

(10) Patent No.: US 11,375,950 B2
(45) Date of Patent: Jul. 5, 2022

(54) SYSTEMS AND METHODS FOR MEASURING RESPIRATORY BIOMETRICS

(71) Applicant: Calibre Biometrics Inc., Wellesley Hills, MA (US)

(72) Inventor: Udi E. Meirav, Waban, MA (US)

(73) Assignee: Calibre Biometrics Inc., Wellesley Hills, MA (US)

( * ) Notice: Subject to any disclaimer, the term of this patent is extended or adjusted under 35 U.S.C. 154(b) by 87 days.

(21) Appl. No.: 16/984,675

(22) Filed: Aug. 4, 2020

(65) Prior Publication Data
US 2021/0085247 A1 Mar. 25, 2021

Related U.S. Application Data

(60) Provisional application No. 62/904,762, filed on Sep. 24, 2019.

(51) Int. Cl.
*A61B 5/083* (2006.01)
*A61B 5/097* (2006.01)
(Continued)

(52) U.S. Cl.
CPC .......... *A61B 5/6803* (2013.01); *A61B 5/0004* (2013.01); *A61B 5/0833* (2013.01);
(Continued)

(58) Field of Classification Search
CPC ... A61B 5/6803; A61B 5/0004; A61B 5/0833; A61B 5/0836; A61B 5/097;
(Continued)

(56) References Cited

U.S. PATENT DOCUMENTS 3,395,701 A * 8/1968 Bartlett, Jr. ............ A62B 27/00
600/532
3,902,516 A * 9/1975 Rudolph ............... F16K 11/105
137/102
(Continued)

FOREIGN PATENT DOCUMENTS

WO WO 2015/124580 A1 8/2015
WO WO 2016/157159 A1 10/2016

OTHER PUBLICATIONS

Mtaweh, H., Tuira, L., Floh, A. A., & Parshuram, C. S. (2018). Indirect Calorimetry: History, Technology, and Application. Frontiers in Pediatrics, 6. doi:10.3389/fped.2018.00257 (Year: 2018).*
(Continued)

*Primary Examiner* — Navin Natnithithadha
(74) *Attorney, Agent, or Firm* — Wolf, Greenfield & Sacks, P.C.

(57) ABSTRACT

Some embodiments are directed to a self-contained breathing mask for measuring and monitoring the breath of a human subject. The mask may be lightweight, self-contained, and physically untethered to any test or measurement equipment, providing the subject full mobility, and allowing him/her to perform almost any daily activity during use. The mask may include integrated sensors for measuring properties of the subject's breath, over any length of time, providing respiratory information like breath count, rate and volume, oxygen consumption, and carbon dioxide production, as well as various biometric information.

19 Claims, 16 Drawing Sheets

Front View

Side View

(51) Int. Cl.
*A61M 16/06* (2006.01)
*A61B 5/00* (2006.01)

(52) U.S. Cl.
CPC ............ *A61B 5/0836* (2013.01); *A61B 5/097* (2013.01); *A61B 2560/0214* (2013.01); *A61B 2560/0257* (2013.01); *A61B 2562/0247* (2013.01); *A61M 16/0616* (2014.02); *A61M 16/0683* (2013.01)

(58) Field of Classification Search
CPC .... A61B 2560/0214; A61B 2560/0257; A61B 2562/0247; A61B 5/083; A61M 16/0616; A61M 16/0683
See application file for complete search history.

(56) References Cited

U.S. PATENT DOCUMENTS

| | | | | |
|---|---|---|---|---|
| 3,964,476 | A * | 6/1976 | Palleni | A61M 16/08 128/205.13 |
| 4,346,584 | A * | 8/1982 | Boehringer | A61B 5/0836 600/532 |
| 5,265,595 | A * | 11/1993 | Rudolph | A61B 5/097 128/204.18 |
| 5,503,151 | A * | 4/1996 | Harnoncourt | A61B 5/087 600/438 |
| 5,572,993 | A * | 11/1996 | Kurome | A61M 16/026 128/204.21 |
| 6,371,110 | B1 * | 4/2002 | Peterson | A62B 18/084 128/202.27 |
| 6,406,435 | B1 * | 6/2002 | Mault | A61B 5/029 600/437 |
| 6,468,222 | B1 * | 10/2002 | Mault | A61B 5/0833 600/529 |
| 2003/0065273 | A1 * | 4/2003 | Mault | A61B 5/222 600/531 |
| 2003/0065274 | A1 | 4/2003 | Mault et al. | |
| 2006/0201511 | A1 * | 9/2006 | Freriks | A62B 17/04 128/206.13 |
| 2006/0254592 | A1 * | 11/2006 | Anders | A62B 23/02 128/206.21 |
| 2007/0255160 | A1 * | 11/2007 | Daly | A61M 16/0605 600/529 |
| 2009/0227887 | A1 * | 9/2009 | Howard | A61B 5/0833 600/531 |
| 2016/0038709 | A1 * | 2/2016 | Beard | A61B 5/097 128/205.12 |
| 2017/0189635 | A1 * | 7/2017 | Beard | A61M 16/0051 |
| 2018/0110951 | A2 * | 4/2018 | Beard | A61M 16/06 |
| 2019/0046746 | A1 * | 2/2019 | Budhiraja | A61M 16/0003 |
| 2019/0070374 | A1 * | 3/2019 | Fogarty | A61M 16/0003 |
| 2020/0016356 | A1 * | 1/2020 | Patel | A61M 16/0683 |
| 2021/0001072 | A1 * | 1/2021 | Lim | A61M 16/0622 |

OTHER PUBLICATIONS

International Search Report and Written Opinion for International Application No. PCT/US2020/044859 dated Oct. 20, 2020.

* cited by examiner

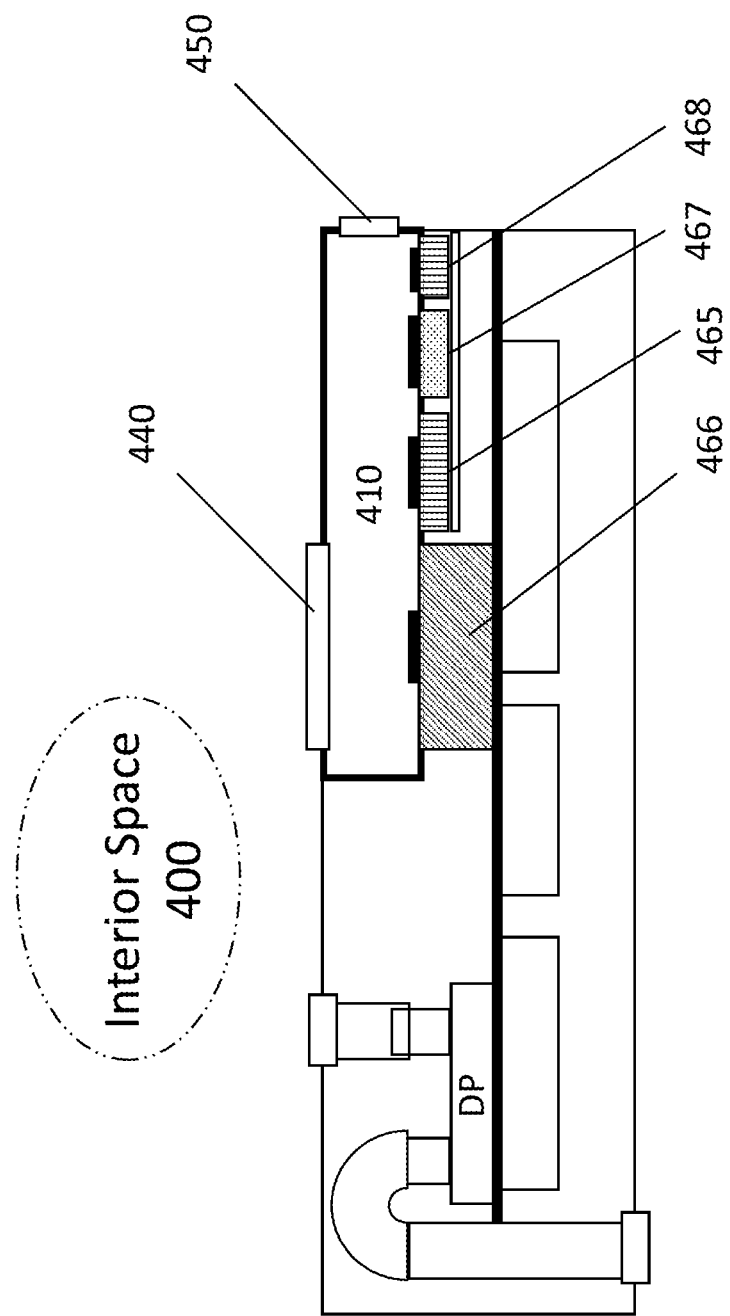

SYSTEMS AND METHODS FOR MEASURING RESPIRATORY BIOMETRICS

CROSS-REFERENCE TO RELATED APPLICATIONS

This application claims priority under 35 U.S.C. § 119(e) to U.S. Provisional Patent Application No. 62/904,762, filed on Sep. 24, 2019, entitled "System for Monitoring Human Breath in Daily Life," the disclosure of which is incorporated herein by reference in its entirety.

TECHNICAL FIELD

Embodiments of the present disclosure generally relate to systems, methods and devices for collecting, analyzing and utilizing respiratory, physiological, metabolic or biometric data.

BACKGROUND

Respiratory air flow volume and composition is rich with biometric and diagnostic information. One example is pulmonary function and the changes in pulmonary function for any individual in response to changes in circumstances, activity or disease. Another example is metabolic information that can be reflected qualitatively and quantitatively by measuring the exchange of gases, and the correlation of this gas exchange to health, nutrition, activity or other circumstances.

SUMMARY

Some embodiments of the invention are directed to a system, configured to be worn by a user substantially on his/her head, for gathering respiratory information about the user. The system comprises a mask and a sensing module. The mask comprises a shell and a seal. The seal is formed of a pliable material arranged to contact a face of the user and to substantially circumscribe an area of the face when the mask is worn by the user. The area of the face includes a mouth of the user and a base of a nose of the user. The seal and the shell substantially enclose an interior space about the area of the face and substantially separate the interior space from an ambient space. The shell comprises a plurality of breathing apertures configured to allow air to flow between the interior space and the ambient space. The sensing module comprises a housing arranged for attachment to the mask. The sensing module comprises gas sensors, air pressure sensors, electronic components, and a battery for powering the gas sensors, the air pressure sensors and the electronic components. The sensing module has a sensing zone with an air flow path from the interior space. The gas sensors are in fluid communication with the sensing zone, and are configured to measure a composition of air exhaled by the user. The air pressure sensors are configured to measure a pressure difference between the interior space and the ambient space. The electronic components are configured to receive data from the gas sensors and the air pressure sensors, and to transmit first information to at least one external device. The first information comprises the received data and/or a result of processing at least a portion of the received data, the processing comprising determining one or more of an inhalation air flow and an exhalation air flow based at least in part upon the measured pressure difference between the interior space and the ambient space.

BRIEF DESCRIPTION OF THE DRAWINGS

FIG. 1A shows front and side views of the representative system, and FIG. 1B shows the system worn on a user's face.

FIG. 4 is a schematic illustration of a cross section of a representative sensing module oriented so that the interior space of the mask is above the module in the example shown.

FIG. 6A depicts inhalation, where air flows inward through the mask apertures in response to a negative differential pressure inside the mask relative to the ambient.

FIG. 6B depicts exhalation, where flow and differential pressure are reversed.

DETAILED DESCRIPTION OF THE INVENTION

Figure 1A:
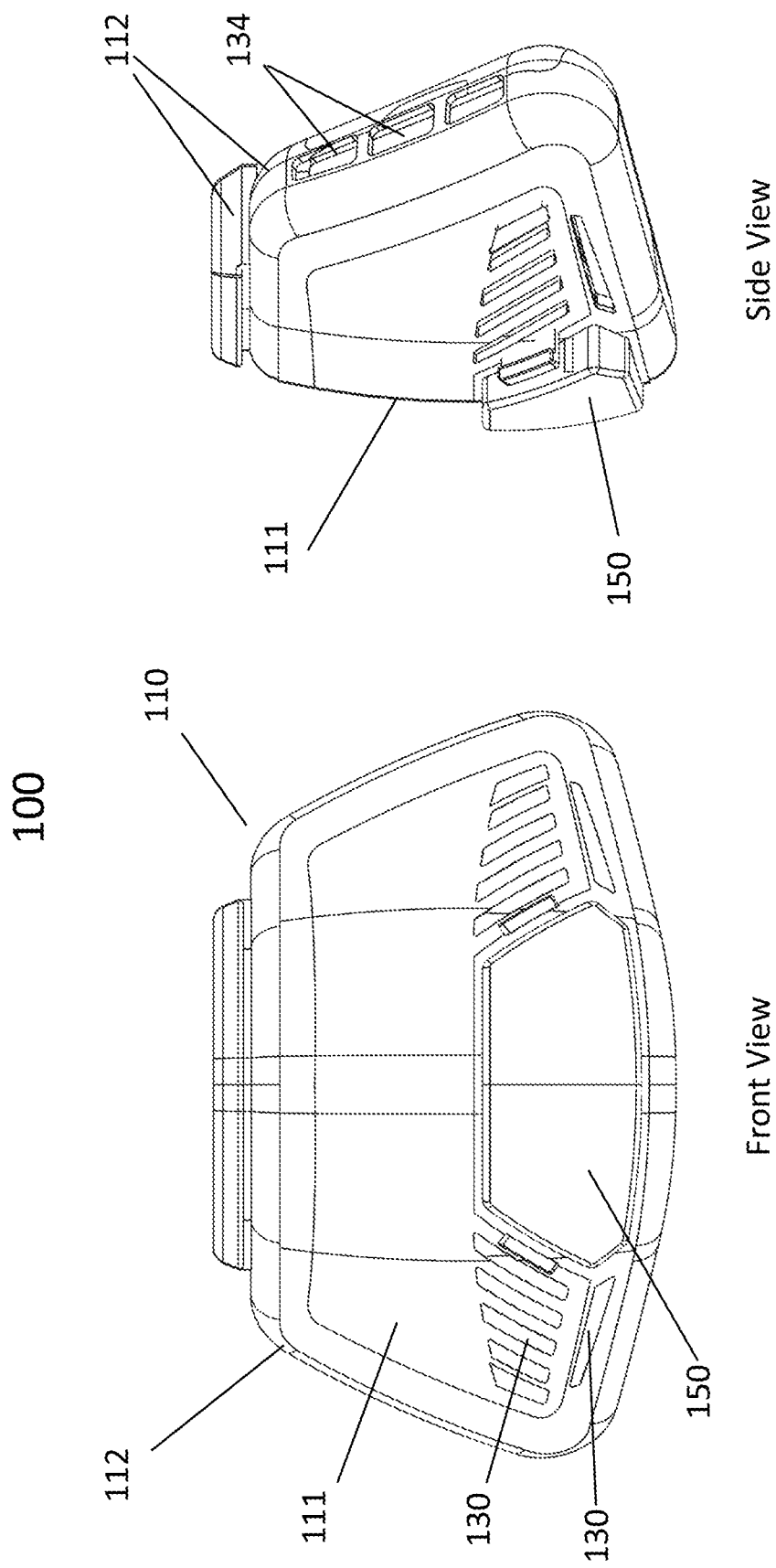
FIGS. 1A-B are schematic illustrations of a representative system implemented in accordance with some embodiments of the present disclosure.

The Applicant has appreciated that measuring the volume and composition of respiratory air flow is a known medical diagnostic technique, but doing so is cumbersome and expensive, requiring the subject to be tethered to analytic instrumentation that is either stationary or unwieldy. The Applicant has also recognized that this makes it impractical to measure such biometrics continuously over a long stretch of time, or to do so in the course of daily life, as opposed to in a limited diagnostic setting, such as in a medical facility or sports laboratory. While some devices can be carried to monitor outdoor athletic activity, these require attachment— by tubes or wires—to instrumentation that is carried by the user, and remain too cumbersome and expensive for widespread, daily use.

Wearable devices for collecting biometric data have become increasingly popular for use by consumers in their daily life. Some are designed to gather biometric data regarding the individual wearing them, for example using motion sensors or contact electrodes. The Applicant has also recognized that some keys to the widespread adoption of wearable devices include a small form factor, comfort and affordability. The Applicant has further appreciated that, to date, there is no wearable device for measuring breath volume and composition having these qualities.

Some embodiments of the invention are directed to systems, apparatuses and methods for measuring and monitoring a person's breath, using a novel type of self-contained breathing mask with integrated sensors. In some embodiments, the mask may be extremely light, and untethered to any test or measurement system—neither electrically nor via tubes—and utilize miniature battery powered sensors and wireless electronics to measure properties of breath continually over any length of time, while allowing the user full mobility and the ability to perform almost any activity while unencumbered and minimally inconvenienced by the device. In some embodiments, data which is collected over periods of time may provide respiratory information like breath count, rate and volume, as well as oxygen consumption and carbon dioxide ($CO_2$) production. These data may be processed to produce information relating to metabolic data, like energy (calories) consumed, or to estimate the fraction of such calories obtained from metabolizing carbohydrates vs. fats, since the two have different $CO_2$-to-oxygen respiratory exchange ratios. In some embodiments, one or more sensors may enable medical or physiological diagnostics and tracking biometrics.

In some embodiments, the system comprises a partially rigid mask that covers the mouth and nostrils, with breathing apertures in the mask and one or more detachable sensing modules. The system may continually determine instantaneous respiratory air flow, such as by measuring a pressure difference between the mask interior and the ambient air. The system may measure the composition of exhaled air in terms of oxygen and $CO_2$ concentrations. Any data that is gathered, generated and/or derived may be conveyed by wireless connection to an external receiving device, such as a mobile phone, or any other suitable computing system(s). The convenience and low cost of such a system may enable respiratory data collection in day to day life, with valuable insight on health and disease, nutrition, metabolism, activity, athletic performance, sleep, etc. Data collected by the system may also be used for medical monitoring, diagnostics, and/or sports medicine. In some embodiments, data gathered by plural systems associated with individual human subjects may provide a research tool, for example allowing the human subjects to be monitored as part of a study.

Figure 1B:
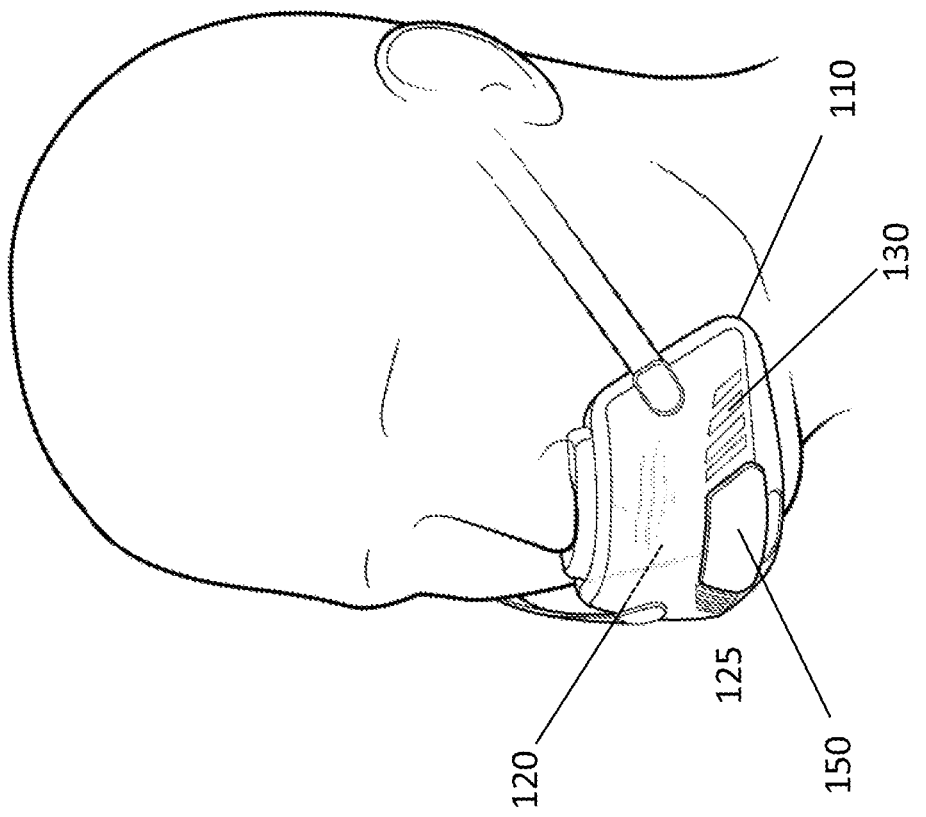

FIGS. 1A-B depict a representative system (100) comprising an exemplary breathing mask (110) configured to be worn by a user, substantially on his/her head. In the representative system 100 shown, mask 110 comprises (i) a firm shell (111) that is designed to essentially maintain its shape when the mask is worn, and (ii) a soft, flexible or otherwise pliable material, also referred to as a cushion (112), along the edges of the mask. In the example shown, the cushion is configured to contact the user's face and substantially circumscribe an area of the face including the mouth and the base of the nose or the nostrils, while conforming to the facial contours, thus substantially preventing air from flowing through gaps between the mask and the skin. When applied to the face (FIG. 1B), example mask 110 may substantially enclose an interior space (120) contained between the mask and the face. The space outside the mask and immediately adjacent to it are referred to herein as the ambient space (125). The mask 110 is further configured with a plurality of geometrically defined apertures or perforations (130) allowing inspired (inhaled) air to flow from the ambient space 125 to the interior space 120, or allowing expired (exhaled) air to flow from the interior space 120 to the ambient space 125. In some embodiments of the invention, a subject's breath does not need to flow through any tubes or conduits for flow rate to be correctly quantified.

It should be appreciated that the mask 110 depicted in FIG. 1 is merely one example, and that a mask implemented in accordance with embodiments of the invention may include any of numerous combinations of elements (only some of which are shown) and/or configurations thereof. As but one example, there may be a wide variety in the design of the apertures in terms of their size, shape, number and location on the mask. In some embodiments, the operation of the system may dictate at least some of the elements and/or configurations thereof, but in some embodiments, the presence and/or configuration thereof may be dictated (at least in part) by other considerations. Some representative operational considerations which may influence design choices are disclosed below.

In certain embodiments, one or more apertures may be configured with "one-directional" flow elements to allow inhalation-only or exhalation-only through these apertures, which are referred to herein as "inhalation apertures" or "exhalation apertures," respectively. In a non-limiting example, a mask may have a plurality of ordinary apertures (130) allowing air flow in both directions, and several additional inhalation apertures (134), to reduce air flow resistance of the mask during inhalation, while maintaining a somewhat higher resistance for exhalation. Some benefits of this arrangement are described below.

Passive one-directional flow valves are known. One example comprises a flexible cover (a "flap") configured to seal the aperture from one side. Positive air pressure from one direction pushes the flap open and allows flow, while pressure from the other direction pushes the flap against the surface, tightening the seal and obstructing flow. Of course, a mask implemented in accordance with embodiments of the invention may include any suitable type(s) of selective flow element(s). Some non-limiting examples are described below.

In the example shown, mask 110 includes a sensing module or subassembly (150) which houses sensors and/or other electronic components. In some embodiments, the sensing module may be contained in a housing that is easily attachable to and/or detachable from the mask. In some embodiments, a plurality of separate sensing modules may be attached to the mask.

Figure 2B:
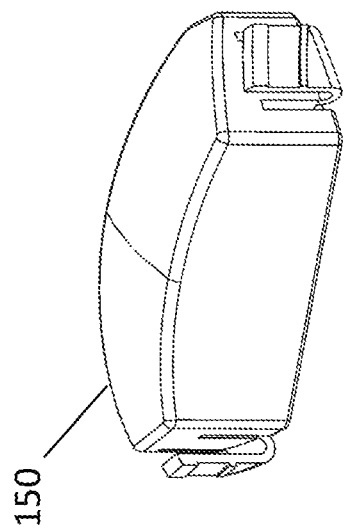
FIGS. 2A-B are schematic illustrations of a representative sensing module detached from the mask, in accordance with some embodiments of the invention.
Figure 2A:
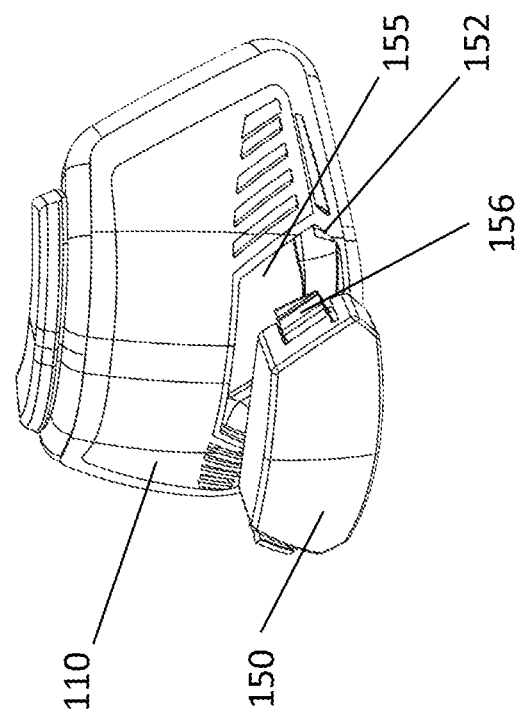
Figure 2C:
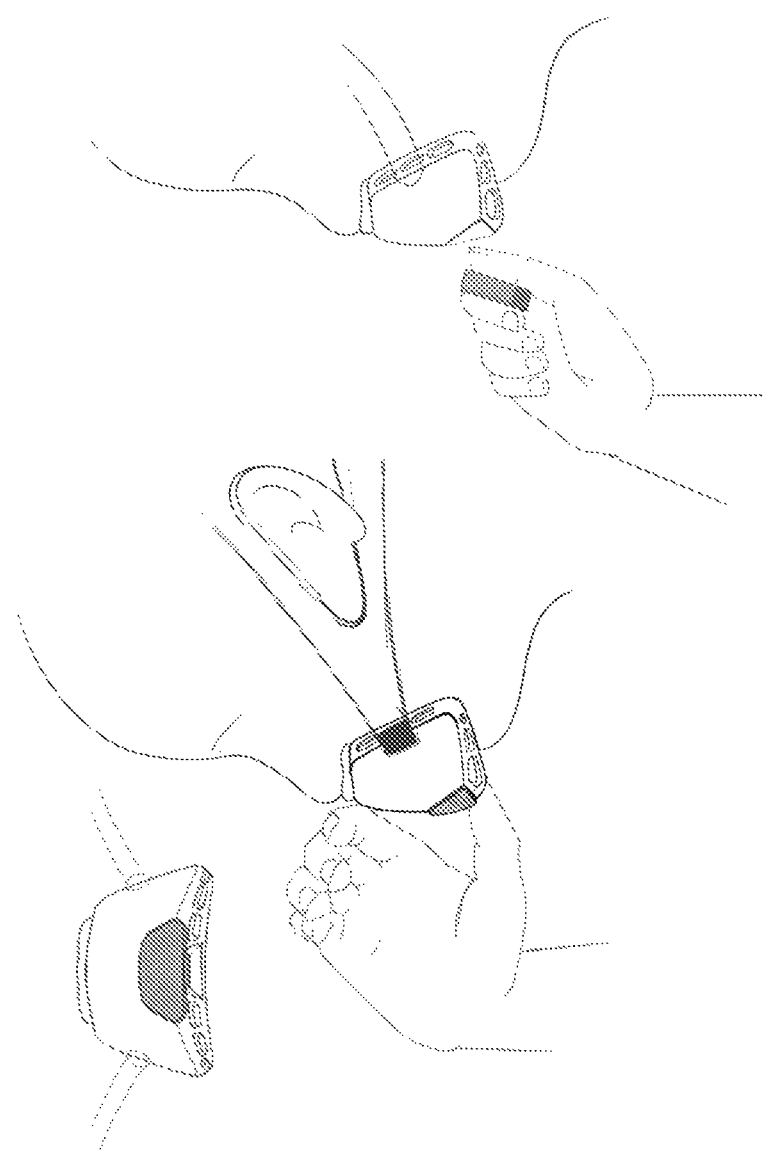
FIG. 2C illustrates one embodiment showing how a user can remove the module while wearing the mask.

FIG. 2A depicts an embodiment of a mask (110) and a sensing module (150) showing the sensing module separated (e.g., detached) from the mask. In some embodiments the housing mates with a feature in the mask (152) which helps to set its position. This can be any feature including but not limited to an opening, a recess, a cavity and a receptacle. In some embodiments the inserted module can be secured in place with the aid of attaching elements, including but not limited to magnets, adhesives, and rigid or flexible mechanical features (156) for holding the housing in place. In some embodiments, the mask is configured with an air-permeable aperture (155) at the location of the module that can allow fluid communication between the mask interior and the module. FIG. 2B shows the module housing as a separate object after removal. FIG. 2C shows how a user can remove and replace the module while wearing the mask In some embodiments, the ability to remove the sensor module from the mask has several possible roles, including but not limited to (a) allowing cleaning or disinfecting the mask, such as with water, detergents, radiation or elevated temperatures, which would damage sensors or electronic components if the module is not removed from the mask before such cleaning; (b) changing or replacing the mask from time to time without necessarily requiring multiple modules, and (c) sharing a module among several users, each equipped with their own mask. It should be appreciated, however, that in some embodiments, the sensing module may not be detachable from the rest of the mask, and that in some embodiments, only a portion of the sensing module (e.g., certain components thereof) may be detachable from the rest of the mask. Embodiments of the invention are not limited to being implemented in any particular way.

Figure 3B:
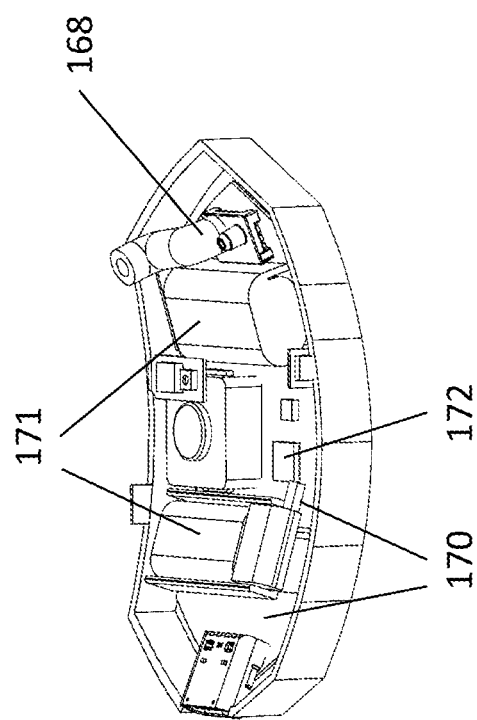
FIGS. 3A-B depict a representative internal layout of an exemplary sensing module implemented in accordance with some embodiments, with some elements omitted to provide better visibility of certain sensors. For example, in FIG. 3A the ports of the differential pressure (DP) sensor are visible, and in FIG. 3B one of the tubes (168) attached to the interior-pressure port is shown.
Figure 3A:
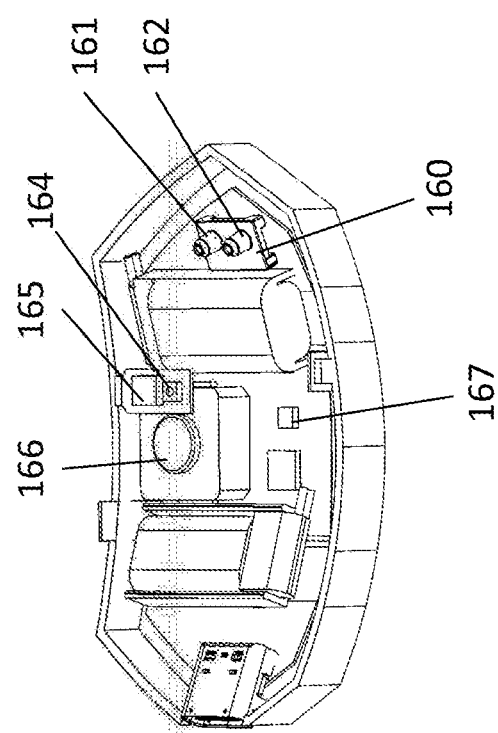

The components of the sensing module can comprise a plurality of sensors, including but not limited to any of pressure sensors, gas sensors, temperature sensors, chemical sensors, electromechanical sensors, optical sensors, accelerometers, and/or humidity sensors. The sensing module may also include one or more batteries and one or more electronic circuits configured to receive sensor readings and/or communicate (e.g., wirelessly) with one or more external systems. FIG. 3A shows a schematic view of a representative sensor module 150 implemented in accordance with embodiments of the invention. The representative sensor module 150 shown comprises a differential pressure sensor (160), a gauge- or barometric-pressure sensor, a humidity sensor (164), a carbon dioxide ($CO_2$) sensor (165) and an oxygen ($O_2$) sensor (166). The system may also, or alternatively, comprise multiple temperature sensors. Some commercially available gas sensors have "built-in" temperature sensors or humidity sensors, thus potentially eliminating the need to incorporate these as separate sensors. The operation of this embodiment will be explained here in further detail; it will be understood, however, that this combination of sensors represents a non-limiting example. It should be appreciated that a sensor module 150 may comprise any suitable number and/or type of sensors. A sensor module implemented in accordance with embodiments of the invention may not include all of the sensors shown in FIGS. 3A-3B, or may include sensors other than those which are depicted in FIGS. 3A-3B. Sensor module 150 may be implemented and configured in any of numerous ways.

In some embodiments, a differential pressure (DP) sensor may be configured with two inlets or ports, shown as 161 and 162 in FIG. 3A. In the example shown, each port is in the form of a short tubular opening extending from the main sensor body. Many differential pressure sensors are available with suitable performance characteristics, such as the Trustability® HSC series available from Honeywell Corp. or the SDP31 series from Sensirion AG (Switzerland), and similar products from NXP Semiconductors (Netherlands), Amphenol Corp., Merit Sensor, and others. In some embodiments the DP sensor is configured so that one of the sensor's inlets is in fluid communication with the interior space, while the other is in fluid communication with the ambient space. Such fluid communication may, for example, be facilitated by a suitable conduit. The conduit can comprise any suitable type, including but not limited to one of flexible tubing, rigid duct, a monolithic part of the housing, or any combination of these. In embodiments that use such a conduit, the open end of the conduit is referred to herein as the "port extension." In some embodiments, the measured pressure may be representative of pressure at the port extension. In the example depicted schematically in FIGS. 3A-3B, the DP sensor has one port (161; FIG. 3A) in communication with the interior space through a conduit (168; FIG. 3B) and a corresponding aperture in the housing; and the other port (162; FIG. 3A) in fluid communication with the external ambient air through a separate conduit (not shown). In this respect, it should be appreciated that in certain embodiments (e.g., those in which the DP sensor is located in a part of the module that is already in fluid communication with one of these spaces—interior space or ambient air), a conduit may not be necessary for a corresponding port.

In some embodiments the instantaneous rate of air flow through the apertures can be determined by measuring DP between the interior space and the ambient air. In doing so, the system may continuously trace a respiratory flow rate (FF) over time. The conversion of DP to FF may be influenced by, for example, the mask structure, including but not limited to the configuration of apertures, as well as the location of the DP sensor port extensions. Given this, in some embodiments, the location of these port extensions may be fixed, so as to produce a predictable and consistent relation between the FF and DP.

Some embodiments may include features designed to account for variations in air flow patterns in the mask interior. In this respect, even for the same person and the same total air flow there can be different flow patterns, for example between nasal vs oral exhalation, or even within oral exhalation with varying positions of the mouth. Moreover, different individuals will often have different facial features that can affect flow patterns. In some subjects, flow patterns can vary more strongly near the mouth and nose. As such, some embodiments may include mask apertures positioned away from the center, and therefore away from the mouth and nose, namely closer to the edges of the mask, such as to reduce flow pattern variations. For example, in some embodiments, the exhalation apertures may be positioned closer to the perimeter or edges of the mask. In some embodiments, an interior sensing port extension may be positioned closer to the edges of the mask. In some embodiments, the interior-space pressure sensing port may be shielded from pressure-flow idiosyncrasies like laminar flow by locating the port inside the module in a section that is in fluid communication with the interior space but shielded from direct flow. Of course, the system is not limited to employing apertures, a sensing port extension, and/or an interior-space pressure sensing port residing in any particular location. In some embodiments, one or more physical features including but not limited to screens, barriers and obstructions may be configured to deflect exhaled air from flowing directly to apertures or to sensors.

Embodiments of the invention may employ any suitable number of sensors of a particular type. As one example, in some embodiments, more than one pressure sensor may be installed. For example, some embodiments may comprise a gauge pressure sensor to measure the absolute or barometric pressure P. The barometric pressure can be used alongside temperature T to correctly convert air volume to mass or to "standard volume" (e.g. standard liters per minute, SLPM). Such conversion requires knowledge of T and P.

As another example, in some embodiments, multiple DP sensors may be used. Employing multiple DP sensors may enable DP to be sensed at multiple locations in the interior space, which may reduce or mitigate flow pattern variations. In some embodiments, module 150 may comprise multiple DP pressure sensors having different ranges and sensitivities, which may (as described in more detail below) afford better accuracy and dynamic range than a single DP sensor.

Some embodiments may employ a compact and low-power oxygen sensor (166) so as to minimize weight, size and battery power consumption. Similar considerations apply to a $CO_2$ sensor and other gas sensors. There are several suitable technologies with commercially available sensors having these characteristics. Miniature $CO_2$ sensors using techniques including but not limited to, non-dispersive infra-red (NDIR) adsorption, photoacoustic effect, and thermal conductivity, are commercially available from multiple vendors in very small form, usually weighing no more than a few grams. Compact oxygen sensors using techniques including but not limited to electrochemical sensors and fluorescence quenching are also available in low cost, low power and light weight forms. In spite of these advantages, embodiments of the invention are not limited to using sensors (oxygen sensors or otherwise) having any particular operating principle, form factor, cost, weight and/or power consumption characteristics.

Certain embodiments have multiple sensors of a similar type, for example two or more oxygen sensors, $CO_2$ sensors, humidity, pressure, or temperature sensors. Sensors may be duplicated for any number of reasons, including but not limited to the ability to provide higher accuracy by combining (e.g., averaging) readings from multiple sensors, and/or providing redundancy or back up in case a certain sensor fails.

In some embodiments, one or more components in the sensing module may be mounted on one or more circuit boards (170), which can be rigid, flexible, or possess a combination or rigid and flexible parts. The representative module shown in FIGS. 3A-3B also comprises one or more batteries (171). In some embodiments a battery may be rechargeable, and the system may comprise an external electrical port for charging the battery. In some embodiments, an electrical port can serve additional purposes, including but not limited to uploading or downloading software or data. The module further comprises electronic circuit components including a wireless communications module (172), and a microprocessor, described in more detail further below. In some embodiments the microprocessor is an integrated part of the communications module.

In some embodiments the sensing module may be divided into a plurality of chambers or compartments, and each of these compartments may be sealed or in fluid communication with other spaces, such as the interior space, the ambient air, or another compartment. In certain embodiments, some components which include components such as a microprocessor, battery, radio transmitter and digital memory may reside in a compartment that is sealed from exhaled air flow. Of course, a sensing module implemented in accordance with embodiments of the invention need not include plural chambers.

Sensing Zone and Optional Vestibule. FIG. 4 shows a schematic cross section of a representative sensing module comprising an oxygen sensor (466), $CO_2$ sensor (465), humidity (467) and temperature (468) sensors configured to measure properties of exhaled air. The sensing module is arranged so that these sensors probe the air in a "sensing zone" (410) that receives exhaled air from the mask interior (400) when the mask is worn. In some embodiments, these sensors may be in fluid communication with (e.g., reside at least partially within) the sensing zone. While in some embodiments the sensing zone may comprise the entire volume of the module, in the example shown, the sensing zone is a confined chamber or section within the module. An inlet (440) provides an air flow path allowing exhaled air to enter the sensing zone. The sensing zone inlet (440) may, for example, include a filter to prevent or reduce the ingress of particles, debris, water condensation or other unwanted components into the sensing zone itself, while allowing gases to enter. Of course, an air flow path allowing exhaled air to enter the sensing zone need not be provided using an inlet which includes a filter, and any suitable arrangement may be used to provide such an air flow path. In the example shown, sensing zone 410 includes an outlet (450) enabling air to flow through the space.

Although only a single sensing zone is shown in FIG. 4, in some embodiments, a plurality of sensing zones may reside in a sensing module. For example, each sensing zone may include different sensors corresponding to that zone. For example, each different sensing zone may receive different amounts of air flow, which can be influenced by any of the apertures, valves or conduits directing air to the zone.

Figure 5:
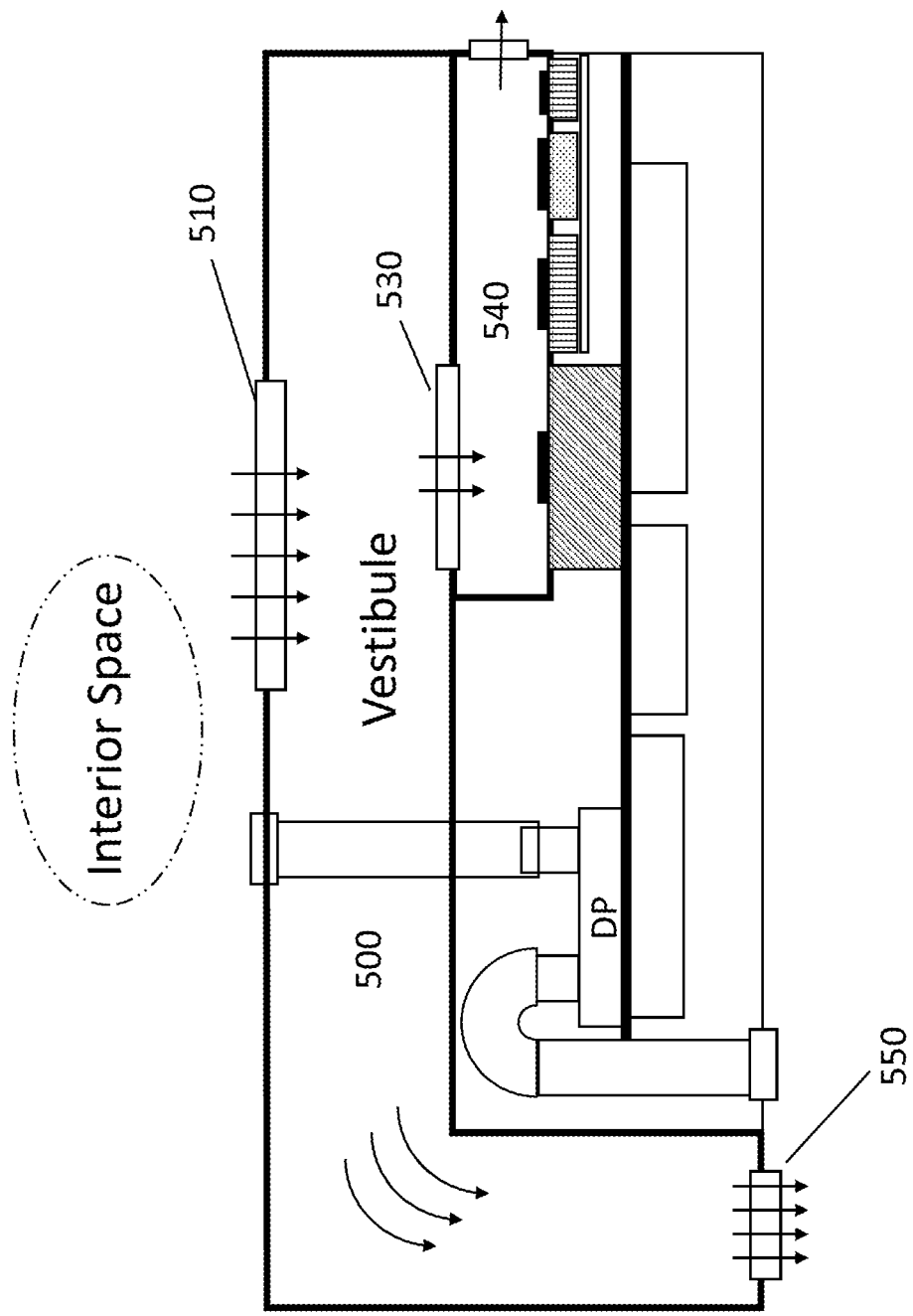
FIG. 5 is a schematic cross-section of a representative sensing module, comprising a vestibule residing between the mask and the sensing space in the example shown.

While in some embodiments air may flow directly from the interior space to the sensing zone, some embodiments may provide for an intermediate space along a flow path from the interior space to the sensing zone, which is depicted schematically in FIG. 5 and referred to herein as a vestibule. In some embodiments which include a vestibule, exhaled air can only reach the sensing zone by first entering the vestibule, and then flowing from the vestibule to the sensing zone. Some potential benefits of the vestibule are described in further detail below. It should be appreciated that although the example shown in FIG. 4 includes a single sensing zone, not all embodiments may include a sensing zone, or even a small number of sensing zones, but instead may include sensors interspersed throughout the system. Embodiments of the invention are not limited to sensors being physically arranged and/or configured in any particular way.

Figure 6B:
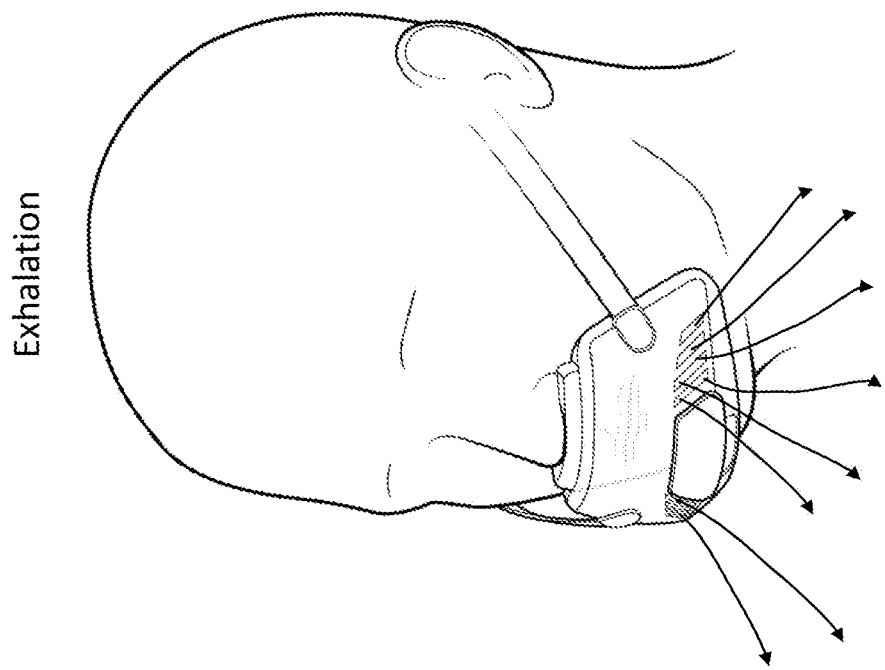
FIGS. 6A-B illustrate how air may flow through the mask during breathing, in accordance with some embodiments.
Figure 6A:
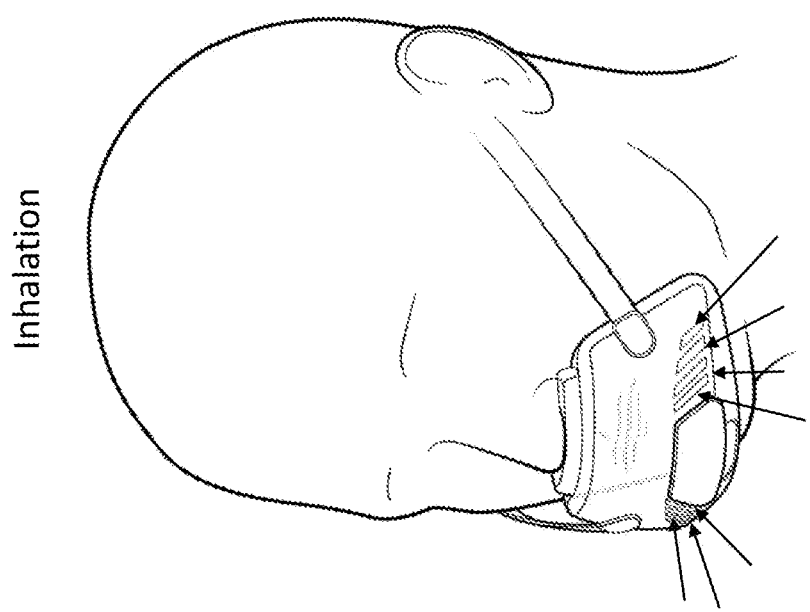

System Operation—Air Flow Measurement. We now turn to explain the operation of some embodiments in measuring respiratory volumes and flow rates. The operation of the system in this embodiment can be explained with the help of FIGS. 6A and 6B, showing inhalation and exhalation, respectively. When the user inhales, low pressure in the lungs pulls air through the mask apertures. If the mask is properly attached, the inhaled ambient air flows substantially through designated breathing apertures rather than through gaps between the mask and the face. The rate of air flow through the mask apertures is determined by a lower pressure in the mask interior relative to the exterior ambient pressure, which is of course created by the lungs and the respiratory muscles. This pressure difference is detected by the DP sensor, which, in some embodiments, has one port inside the mask and the other outside the mask.

Similarly, when the user exhales, high pressure is produced by the lungs and the air flows out through the designated apertures to the ambient. The air flow is induced and determined by a pressure difference DP that is caused by the (even higher) pressure in the lungs. It is measured by the DP sensors described earlier, and the measured value is received by the electronic circuit, and may be processed, stored and/or transmitted.

The pressure sensor(s) effectively measures this pressure difference between the interior mask pressure, $P_i$, and the ambient pressure outside of the mask, $P_a$.

$$DP=P_i-P_a$$

A consistent mathematical relationship exists between the respiratory air flow FF and the DP measurement. This pressure-velocity relationship can be approximately linear at low rates, and in any case a fixed property of any particular mask & aperture design. It need not be symmetrical or precisely linear, but as long as it is consistent, monotonic and well calibrated, it can be used to convert DP readings to FF for that particular mask design.

Typical human tidal breathing comprises approximately 12-15 inhalation and exhalation cycles per minute, and each cycle for an average adult male is around 0.5 liters of air. However, breath frequency and volume can be much higher under physical exertion. To measure breath volume accurately, the flow—hence the DP—should be measured in sufficiently high time resolution so as to capture the oscillating changes in flow rate with adequate fidelity. In other words, the DP readings should be recorded at high reading rate relative to the breathing frequency. Fortunately, typical DP sensors have reading rates much faster than even the most elevated human breathing rate. Sensors specified at 1 millisecond reading time, namely a 1 kHz rate, are fairly common. In some embodiments the DP sensor values are recorded at a frequency between 10-100 readings per second, which is often suitable. In some embodiments, DP sensor readings are taken at a frequency between 100-1000 per second. In some embodiments readings are taken at a rates lower than 10 per second. In some embodiments, readings are taken at a rate higher than 1000 per second. In some embodiments readings are taken at a variable frequency, based on the read values and their rate of change.

In some embodiments the exact relationship between DP and FF can be established by testing or simulation and then stored and used as a conversion table, a parametric formula, or a hybrid conversion that uses a plurality of piecewise conversion formulas, each applying to a certain range of values of DP. In the case of a table, values that are not specifically represented on the table can be converted by interpolation between available values or rounded to the nearest available value. In some embodiments a parametric formula can be as simple as linear conversion $$FF=a_1DP$$

or a power series expansion such as $$FF=a_1DP+a_2DP^2+a_3DP^3+\ldots$$

Where $a_1$, $a_2$ etc. are the conversion coefficients.

The conversion of DP to FF can be performed by the sensing module, and/or after transmission (e.g., by a receiving device). If the conversion is performed by the sensing module, in some embodiments a microprocessor in the sensing module may perform the conversion, such as using a conversion table, or coefficients, stored in memory. In some embodiments, the DP readings themselves may be transmitted—directly or indirectly—to a separate computing system, the latter being programmed to perform the conversion and supplied with the required tables, coefficients or formulas.

In some embodiments, frequent recalibration of the zero point of a DP sensor can reduce measurement errors. Such recalibration can be performed by measurement of the DP when there is no air flow at all, such as when the mask is not worn or the module is detached from the mask, as shown schematically in FIG. 2.

In some embodiments the size, number and configuration of the apertures may affect DP during breathing. As a non-limiting example, if the apertures are relatively smaller or fewer, then DP readings might be larger and easier to measure, but breathing may be relatively restricted, especially under exertion and athletic activity. By contrast, if the apertures are relatively wide or numerous, breathing may be easier, but DP values may be smaller and more difficult to measure accurately. As such, DP reading considerations may influence the design of the apertures.

Variable Apertures. In some embodiments, variable apertures can be used to allow for different operating modes. In a non-limiting example, one or more apertures can be configured with a cover or seal that can be opened manually by the user or electronically by the module. When the variable apertures are closed, the system may be better suited for ordinary breathing rates, providing relatively higher resistance and therefore easier to accurately measure DP at low air flow rates. Conversely, when some or all of the variable apertures are open, the system may be better suited for higher breathing rates, for example during exercise or hard work.

In some embodiments, some or all of the variable apertures may allow for plural settings, including settings labeled as open/closed, high/low, or using any other suitable nomenclature. In some embodiments the system enables more than two settings or operating states. These multiple states may be realized, for example, by partially opening or closing certain apertures. In some embodiments, multiple operational states may be realized using a multistate seal on one or more apertures. A non-limiting example of a seal is a sliding cover that can gradually cover or reveal a portion of an aperture.

In some embodiments, some or all of any variable apertures may be controlled physically by the user, such as by moving or removing appropriate covers as needed. In some embodiments, some or all of any variable apertures may be activated electronically by the system. In some embodiments the system can be programmed to change the settings for one or more of any variable apertures in response to a user request. In some embodiments the system may modify settings for one or more of any variable apertures based on circumstances (e.g., detected by the system). In a non-limiting example, the system may modify settings for one or more of any variable apertures in response to a measured flow rate or a breathing frequency.

In some embodiments with variable apertures, the conversion of DP to FF is informed by the settings of certain apertures and the system registers the latter to properly calculate FF. In some embodiments, the settings may be provided to the system by the user. In some embodiments the settings determined or detected independently by the system through any suitable means, including but not limited to magnetic, mechanical or optical sensors.

In some embodiments, if the mask does not seal well against the face, air can flow through gaps between the mask and the face during inhalation or exhalation, which is referred to herein as leakage. Such leakage may undermine the equality between the aperture air flow and the total respiratory air flow. The cushion of the mask may play an important role in sealing and minimizing leakage. Some designs may be prone to leakage in one direction (inhalation or exhalation) but not both; since the volume of inhaled and exhaled air are similar, in some embodiments sealing that is effective for only one direction may therefore be sufficient.

In some embodiments, only exhaled air flow rate may be recorded and used for computing biometric quantities. Such embodiments may benefit from adding one-way inhalation apertures that further reduce inhalation pressure differentials, thereby increasing inhalation comfort without undermining flow measurement accuracy at low exhalation rates. In some embodiments, only inhaled air volume may be recorded and used for computing biometric quantities, with parallel benefits. In some embodiments, both inhaled and exhaled air may be used for computing biometric quantities.

Alternative Techniques to Measure Air Flow. It should be appreciated that measuring DP between ambient air and the interior space using fixed apertures is not the only way to determine air flow in the system. Any of numerous techniques may be used for measuring air flow to determine respiratory flow rate. In some embodiments air flow may be measured by directing air to flow through a permeable screen. In some of these embodiments, the flow resistance properties of the screen convert flow to DP, and in some embodiments the measurement of DP can be used to estimate flow. In some embodiments, air flow may be measured by a small turbine or rotating fan that turns as air flows through it, for example by measuring the rate at which the turbine turns. In some embodiments, a heated element may be placed in the flow path, and its temperature or rate of heat loss can be used to measure air flow. In some embodiments a Venturi element is configured in the flow path of the air to measure the flow rate, using the Venturi principle. Any suitable technique for measuring flow may be used, as embodiments of the invention are not limited to employing any particular technique. Considerations outlined above for the air flow measurement can be applied or translated to other techniques by individuals skilled in the art.

System Operation—Composition of Exhaled Air. The respiratory consumption of oxygen over time is the cumulative difference between inhaled oxygen and exhaled oxygen over that time. The relative concentration of oxygen in ambient (inhaled) air is usually stable and rarely deviates significantly from its atmospheric vale of ~20.95%. Similarly, the respiratory release of $CO_2$ is the difference between exhaled amount and inhaled amount, but $CO_2$ concentrations in ambient (inhaled) air are negligibly low—typically 0.04% outdoors and usually no more than 2-3 times higher indoors, which is still negligible compared with about 4-5% $CO_2$ that is typical of exhaled air, and for most purposes can be ignored. In some embodiments, the fixed composition of inhaled air can be used in various ways to facilitate the quantification of respiratory gas exchange.

In certain embodiments, inhaled air and exhaled air may constantly mix and replace each other in the interior space of the mask. Different approaches can be used to separately determine exhaled air composition in such embodiments, and several non-limiting examples are described herein: (a) Isolating a separate stream of exhaled air and measuring its composition, an approach referred to herein as "Separated Exhaled Air Sensing" (SEAS), (b) Measuring the composition of a balanced mix of both inhaled and exhaled air in the mask and mathematically extracting the average value of oxygen and $CO_2$ concentrations in the exhaled air, which is referred to herein as "Mixed Air Sensing" (MAS), and (c) Using sensors with sufficiently fast response time to measure rapid changes in concentration and correlate measured concentrations with the respiratory cycle to isolate the properties of exhaled air, which is referred to herein as "Time Resolved Air Sensing" (TRAS). A more detailed discussion of these techniques follows. Beyond these example, other suitable methods may be used with appropriate adjustments to the system itself and the data analysis.

Figure 7A:
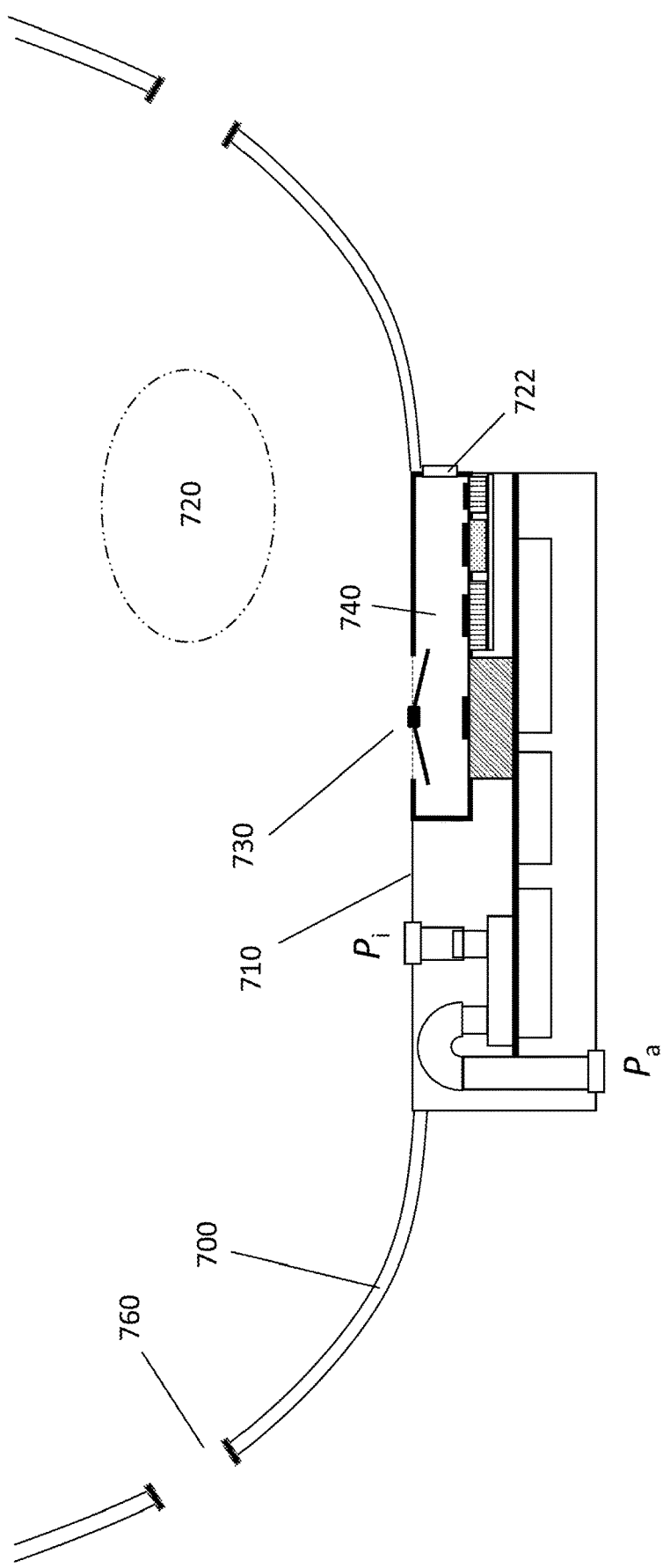
FIGS. 7A-C are schematic illustrations of a representative apparatus and technique for SEAS (Separated Exhaled Air Sensing), in accordance with some embodiments of the invention.
Figure 7B:
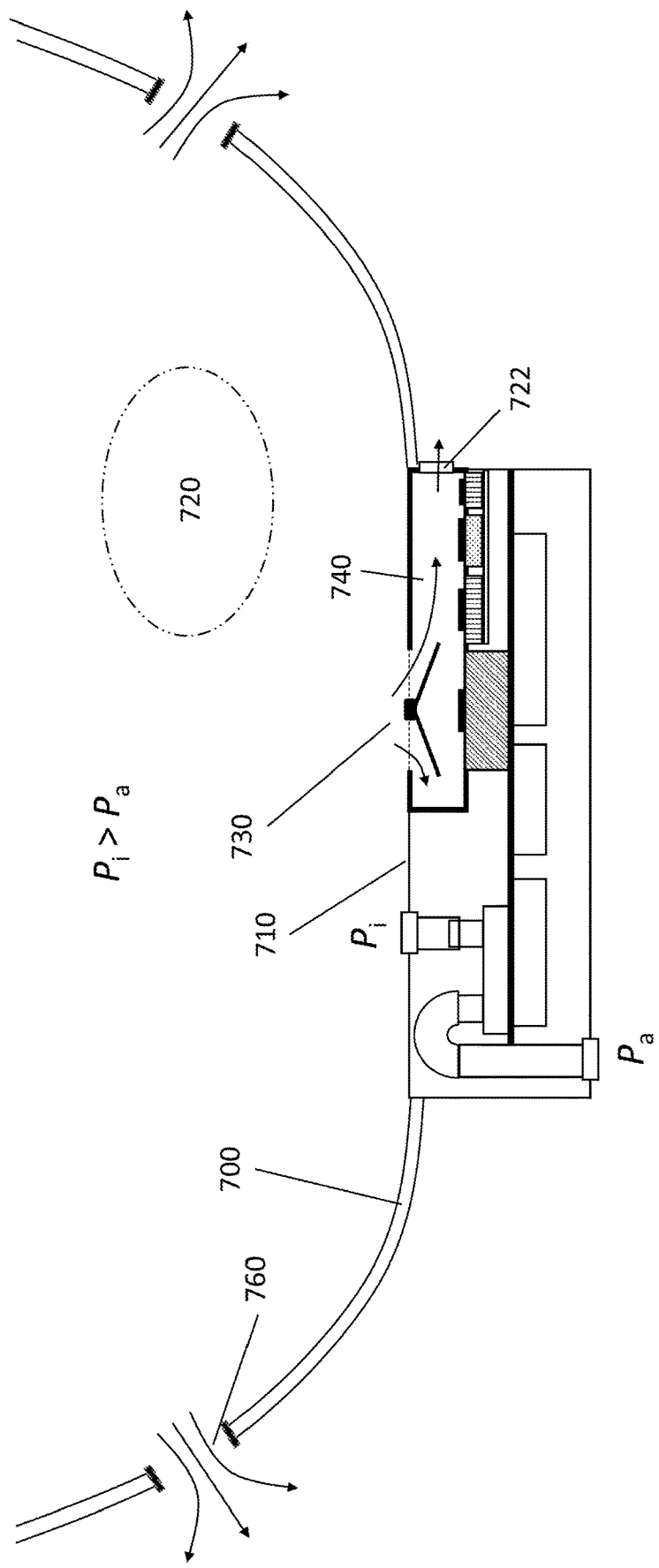

Separated Exhaled Air Sensing (SEAS). FIG. 7A shows a schematic view of a representative technique and apparatus for performing SEAS. In the example shown, a mask (700) is configured with apertures (760) and a sensing module (710) attached to the mask. The sensing module comprises a selective flow element (730) which allows air to flow from the mask interior (720) to the module's sensing zone (740), but not the other way. In this embodiment the selective flow element is "upstream" from the sensing zone, where "upstream" should be understood in reference to the flow direction during exhalation. Flow may be further facilitated by an optional exit aperture (722) allowing air to flow out of the sensing zone as more exhaled air comes in. FIG. 7B adds arrows to depict air flow during exhalation, when the pressure $P_i$ in the mask interior is higher than the pressure in the ambient $P_a$, namely DP is positive. Exhaled air exits the mask, primarily through the mask apertures (760), but also some exhaled air flows through the selective element (730) into the sensing zone (740). In the example shown, some air from the sensing zone flows out to the ambient through the exit aperture (722).

Figure 7C:
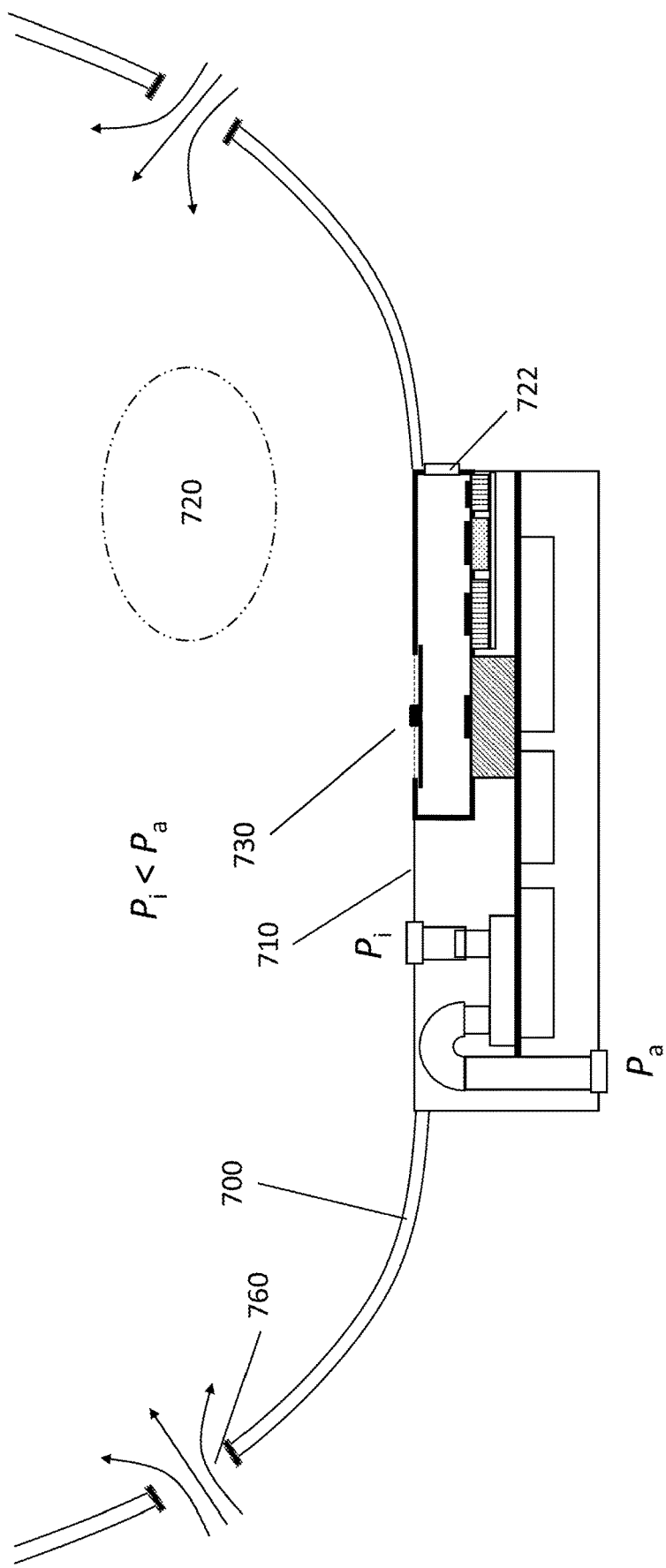

In the same embodiment during inhalation, the interior pressure is lower than the ambient, namely DP is negative, shown in FIG. 7C. In the example shown, this causes the selective flow element (730) to block flow and prevent substantial ingress of ambient outside air into the sensing zone. The result is that over the course of one or more respiratory cycles, the sensing zone continuously senses exhaled air and not a mix of exhaled air and ambient air.

In some embodiments, the amount of exhaled air entering the sensing zone during exhalation may be only a small fraction of the total exhaled air and may not be constant. In some embodiments that fraction is less than 1%. In some embodiments the fraction is between 1% and 10%. In some embodiments the fraction is not constant and varies with exhalation flow rate and volume. In some embodiments a significant portion of the exhaled air flows through the sensing zone. In some embodiments the FF vs DP relationship may be calibrated to take into account the amount of exhaled air flowing to the sensing zone.

In some embodiments which employ SEAS, a selective flow element may also, or alternatively, be located "downstream" of the sensing zone. One non-limiting example is near the sensing zone exit aperture (722). This element may prevent ambient air from entering the sensing zone when the pressure differential is reversed under inhalation. In some embodiments the selective element in (722) may be placed in addition to an element located upstream (730), between the mask and the sensing zone, whereby the sensing zone is effectively "sandwiched" between two selective flow elements.

Any suitable type(s) of element(s) may be used to selectively permit air flow, whether now known or later developed. In some embodiments, the elements are passive one-way flow valves. One example of such a valve comprises a flexible flap configured to cover an aperture in such a way that pressure and flow in the "open" direction pushes the flap aside and allows air passage, and pressure from the other direction tightens the flap to seal the aperture.

Some embodiments may employ electrically controlled active selective flow elements that are synchronized or coordinated with the DP sensor readings so as to open for air flow only during exhalation, as determined by the positive DP. The mechanism can be piezoelectric, magnetic, electrostatic, or use any electric motor or actuator. In some embodiments, such active control allows the system to be programmed to vary the size of certain apertures and/or the amount of time that certain apertures remain at a particular size. In some embodiments, active control of the selective flow apertures may be used to manage the timing, duration or the amount of air entering the sensing zone, for any purpose. In a non-limiting example, active control may be programmed to sample air selectively from a particular phase or stage in each breathing cycle. In another non-limiting example, active control may be programmed to compensate for changes in breathing rate by increasing the opening during slow breathing or decreasing it during heavier breathing.

In some embodiments the sensors of the sensing zone are in fluid communication with the exhaled air entering the sensing zone, and provide multiple readings at some frequency, which readings are passed to digital components of the electronic circuit, including but not limited to a microprocessor, which may process, store, and/or transmit the readings (and/or other information, including results of processing the readings) to one or more external devices. In some embodiments the reading frequency may be between 30-60 per minute. In some embodiments the reading frequency may be less than 30 per minute. In some embodiments the reading frequency may be higher than 60 per minute. In this respect, the benefit of an increased reading frequency may be diminished by a number of factors, including but not limited to (a) an inherent response time of a gas sensor, (b) a diffusion or mixing time of exhaled air entering the sensing zone, and (c) longer time constants associated with the physiology of certain biometric variables. Regardless, it should be appreciated that readings may be performed at any suitable reading frequency. It should further be appreciated that embodiments of the invention are not limited to employing the representative apparatus and/or technique shown in FIGS. 7A-7C to perform SEAS, as any suitable apparatus may be used, to perform any suitable technique(s) relating to measuring separated exhaled air. Some variations on the representative apparatus and technique shown in FIGS. 7A-7C are described below, and involve minimizing humidity, and the use of a vestibule. However, any of numerous other variations may be performed. Embodiments of the invention are not limited in this respect.

Humidity Condensation. Because exhaled air has high relative humidity (RH) and water content, and because exhaled air is often warmer than the ambient and the module components, some embodiments may employ techniques for minimizing the condensation of water on parts of the module, which over time may interfere with their proper operation. In some embodiments, water condensation may be minimized by limiting the amount of exhaled air passing through the module, such as by configuring the components that direct exhaled air to the sensing zone. In some embodiments, the amount of exhaled air passing through the module may be controlled at least in part by active flow elements.

Other techniques can be implemented to mitigate condensation, including but not limited to (i) incorporating desiccants or hydrophobic materials to protect sensitive components and (ii) elevating the temperature of some parts of the module. In some embodiments heat from the exhaled breath or the skin is transferred to elevate the temperature of parts of the module. In some embodiments the heat transfer is facilitated by one or more heat transfer elements, a non-limiting example of which is a metallic surface embedded in the module housing and facing the interior of the mask.

Vestibule. In some embodiments, a vestibule, as described above with reference to FIG. 5, may receive exhaled air prior to it reaching the sensing zone. In the example shown in FIG. 5, an inlet (510) allows exhaled air to enter the vestibule space (500), and a first aperture or channel (530) allows air to flow from the vestibule to the sensing zone (540). In some embodiments the vestibule can be further configured with one or more separate outlets (550) that may allow exhaled air to flow to the ambient air. In some embodiments a vestibule may comprise selective flow elements in at least one of (510) and (550), configured to enable only exhaled air to flow into the vestibule, from which it can also diffuse or flow into the sensing zone. In some embodiments, any aperture, including (510) and (530) may further comprise a filter to protect the sensing zone from ingress of particles, fluids or contaminants. In some embodiments the vestibule may be an integral part of the part of the mask, whereas in some embodiments the vestibule may be part of the detachable module. The incorporation of a vestibule into the module may provide several advantages, including but not limited acting as a buffer space, or allowing large variations in the amounts of exhaled air to flow through vestibule, depending on the breathing rate, while maintaining relatively small flow of air into the sensing zone.

Figure 8:
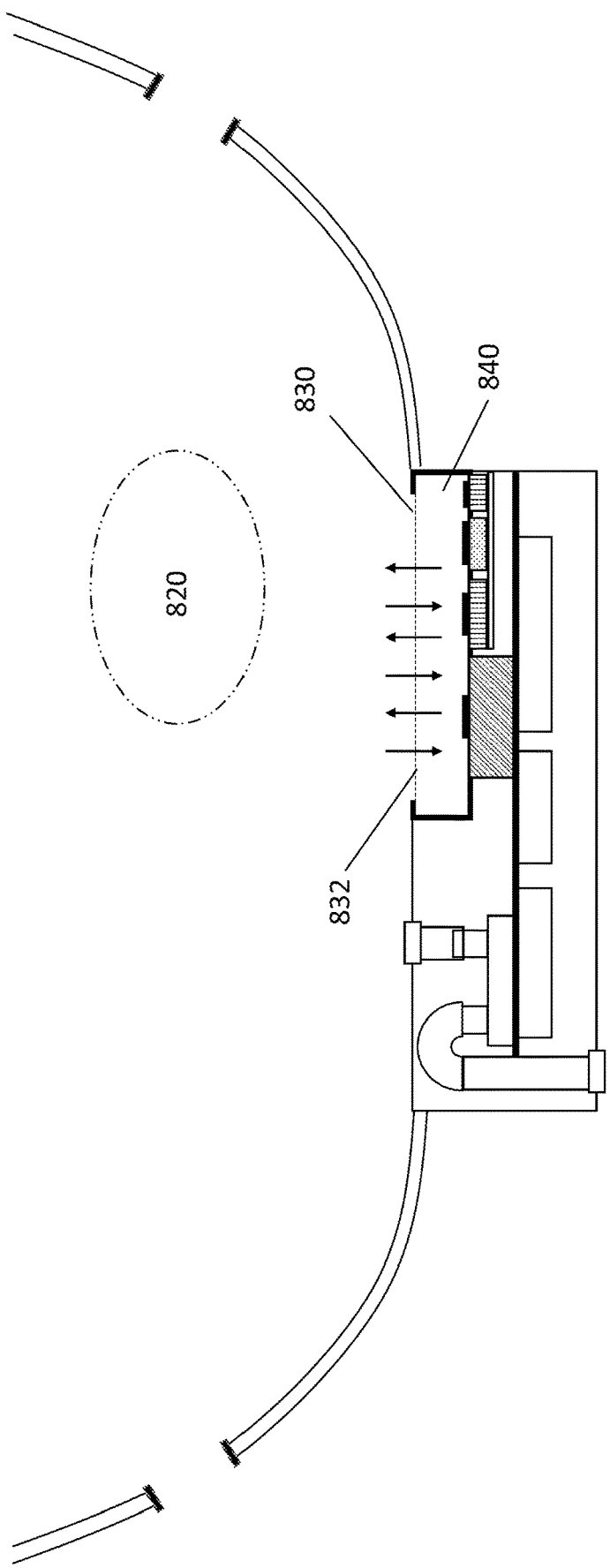
FIG. 8 is a schematic illustration of a representative apparatus and technique for MAS (Mixed Air Sensing), in accordance with some embodiments of the invention.

Mixed Air Sensing (MAS). In some embodiments the system is configured such that the sensing zone is exposed to both inhaled air and exhaled air in similar amounts or at a known ratio between inhaled and exhaled air entering the sensing zone. FIG. 8 is a schematic view depicting a representative apparatus and technique for MAS, where an aperture (830) is configured between the mask interior space (820) and the sensing zone (840). In the example shown in FIG. 8, the opening (830) is not directionally selective and air can pass in either direction at any time including during inhalation and exhalation, although the use of MAS does not necessarily preclude the use of selective flow elements. In some embodiments the opening may be protected with a permeable screen or filter (832). The air composition reaching the plurality of sensors may vary over the course of each breathing cycle, but, in certain embodiments, the time-averaged composition is a mix of substantially equal amounts of inhaled and exhaled air.

In some embodiments the concentration sensors are substantially linear in the range of interest between inhaled and exhaled air, whereby the value X of a specific gas component concentration (e.g. oxygen, $CO_2$, humidity) averaged over a breathing cycle can be determined by averaging the corresponding sensor readings over the cycle:

$$\langle X \rangle = \frac{\int_0^T X(t) \partial t}{T}$$

And if the exposure to inhaled and exhaled air is quantitatively balanced, then $$\langle X \rangle = \frac{X_i + \langle X \rangle_e}{2}$$

Where the constant value for inhaled (ambient) air $X_i$ is approximately known, or alternatively is established by baseline calibration procedure. As explained earlier, ambient oxygen can be simply approximated to be its known typical value in atmospheric air, and ambient $CO_2$ can similarly be approximated based on known values, which are practically negligible. In some embodiment humidity can be a part of some biometric calculations, and in some embodiments a separate humidity sensor measures ambient humidity. The mixed-air measurement can be used to extract exhaled values simply as follows:

$$\langle X \rangle_{e=2} \langle X \rangle - X_i$$

In some embodiments, the amount of inhaled and exhaled air entering the sensing zone over each cycle are not equal. The formula can be generalized to mixed air sensing where these are not equal but their ratio is known or may be approximated. In some embodiments it can also be generalized to account for non-linearity of one or more sensors. In some embodiments, the ability to impute the exhaled air composition from the mixed air measurements can enable some simplifications in the physical design of the MAS system. One non-limiting example is the elimination of a selective flow element from the air path between the interior and the sensing zone. It should be appreciated that the apparatus and technique shown in FIG. 8 is merely exemplary, and that any suitable apparatus and/or technique(s) may be used to perform mixed air sensing. Embodiments of the invention are not limited in this respect.

Time-resolved Air Sensing. In some embodiments the gas sensors may not rely on physical mixing or physical separation of inhalation and exhalation, but on fast-resolution readings of the air composition. In some embodiments the sensor readings may be collected continuously along with the DP readings, which allows the system to associate them separately with inhalation or exhalation; in some embodiments, exhalation corresponds to positive DP in the interior relative to the ambient, while negative DP corresponds to inhalation. In some embodiments the exhaled air concentration values can be averaged to obtain the values required for biometric calculations. In some embodiments a certain (e.g., predetermined) time delay can be taken into account between the onset of positive DP and the inclusion of sensor readings for the purpose of representing exhaled air, this delay representing, for example, a combination of one or more of (i) intrinsic sensor response time; (ii) flow or diffusion time in sensing module; (iii) displacement of ambient air in the interior at the end of inhalation, or any other source of delay including physiological. It should be appreciated, however, that any suitable technique(s) may be used to perform time-resolved air sensing. Embodiments of the invention are not limited in this respect.

Ambient Conditions. In some embodiments the ambient conditions including but not limited to any of temperature, barometric pressure and humidity (absolute or relative) may be measured by the system. These values can be used for any number of biometric calculations. A non-limiting example would be to correctly relate volume and mass of air flow, as the mass density of the air varies with barometric pressure (P) and temperature (T). Generally, the density of a gas, namely mass to volume ratio, increases with pressure and decreases with temperature, according to the ideal gas law $PV=nRT$ (where n is the amount of gas, in moles, and R is the ideal gas constant). To convert gas volume to mass it is useful to measure, or to estimate, the ambient pressure (affecting both inhaled and exhaled air) and ambient temperature (primarily for inhaled air). The ambient pressure generally depends on altitude, and can further vary with weather patterns and can also be influenced, for example, by indoor mechanical ventilation systems. Naturally temperature will vary between indoors, outdoors and weather or climate conditions. In some embodiments, ambient pressure and temperature are obtained from another system or network via wireless communication, including but not limited to publicly available meteorological information and indoor climate monitoring systems.

In some embodiments the relative composition and density of the ambient (inhaled) air may be used for computing certain respiratory and metabolic quantities. In some embodiments, ambient air composition can be estimated simply as the typical composition of dry atmospheric air, which is 20.95% oxygen, 0.04% $CO_2$, with the remainder mostly being metabolically inert nitrogen (~78%) and argon (~0.9%). These values can be corrected for humidity, which itself can be approximated, and/or received from an external information source. In some embodiments, concentration properties of ambient air, including but not limited to concentrations of oxygen, $CO_2$ or humidity, are measured by sensors that are part of the system.

In some embodiments the sensing module comprises sensors in physical communications with the ambient air, to determine P and T. These values can be updated at any suitable frequency. In some embodiments ambient properties are measured when triggered by an action taken by the user. In some embodiments an ambient sensor can be thermally insulated from exhaled breath or other sources of body heat.

In some embodiments the composition of the ambient air can be determined by the sensing module when it is not exposed to respiration. As a non-limiting example, this can be part of a calibration procedure that is run when the module is not attached to the mask, as shown schematically in FIG. 2, or when the mask is removed from the user's face. In some embodiments the calibration procedure can be initiated by the user, for example by pressing a button on the module, or by requesting a calibration from a program that is in wireless communications with the module.

In some embodiments the calibration of pressure can be substituted with a determination of altitude which can be provided, for example, by satellite based global positioning system (GPS), a cellular network or an external barometer. In some embodiments the GPS receiver can be incorporated into the subassembly itself. In other embodiments the system can rely on a mobile phone or another wireless device to determine the altitude or pressure through its own GPS capability, barometer, or other means of determining altitude.

Other Sensors. Additional sensors can be added to detect other physical or biometric parameters of interest that can complement the biometric information imputed from the analysis of the breath. In some embodiments, other molecular components of the exhaled air, including ketones, alcohols, ammonia or any other chemical species can be measured by incorporating suitable sensors into the sensor subassembly. In some embodiments electrochemical sensors are used to detect certain molecular species, including alcohols, in breath. In other embodiments suitable sensors can trace ketones in the breath, which can be indicative of ketosis or diabetes. Ammonia can occur in breath in association with kidney disease or liver disease.

In other embodiments, electronic, electro-optical and/or micro-electro-mechanical (MEMS) sensors may be incorporated in the system to provide complementary biometric information, including but not limited to heartbeat, blood properties, and motion or acceleration (such as step counters for monitoring walking or running). In another embodiment a GPS receiver is incorporated into the system, allowing the user to associate biometric data with physical location.

In some embodiments the accuracy of certain calorimetric data may be influenced by the accuracy of the air flow measurement. For example, the DP sensing may require accuracy over a wide dynamic range of potential respiratory flow rates that can be difficult to address with a single sensor. In some embodiments, the system comprises multiple pressure sensors with different dynamic ranges or sensitivities to improve accuracy. As a non-limiting example for illustrative purposes only, the system may have two sensors, one ranging up to 250 pascals, the other having a wider dynamic range up to 2000 pascals but with lower sensitivity. When the user is sedentary and breathing slowly, typical mask DP readings may be below 10 pascals throughout the breathing cycle and the higher range sensor readings are ignored. Under high exertion, readings may go above 250 pascals, where the lower scale sensor is off scale and ignored. In the range between, say 10 pascals and 250 pascals, the system may take a weighted average of the readings with the relative weight varying with the reading values.

Mask Design Considerations. Protective breathing masks are known in the art, typically covering much of the face from the bridge of the nose to the chin or the lower jaw. In certain instances these attach rather firmly to the face (to prevent air leakage around the mask edge) or in contact with the mouth, rendering them potentially uncomfortable for extended use and otherwise disruptive for the user. In some embodiments of the current invention, the mask seals around the mouth and the base of the nose, namely the bottom of the nasal ala and the nasal tip, as shown in FIG. 1B. This may keep the entire bridge of the nose uncovered and visible, as well as the cheeks, chin and lower jaw. The user can apply the mask while wearing glasses and can speak comfortably.

The shell can be made of any suitable material including but not limited to plastics, resins, composites, fiber based materials, metals, ceramics and plant derivatives. In some embodiments, the shell is substantially transparent. In some embodiments, the shell is rigid and maintains its form under ordinary usage. In some embodiments the firm structure provides a robust DP vs FF relationship as explained earlier. In some embodiments the firm structure is configured to avoid contact with the lips and not impede speech. A thinner shell wall may generally provide for lower weight. In some embodiments a thin shell is reinforced with ribs, spines or other skeletal and/or topographical features. In some embodiments the shell is water resistant. In some embodiments the shell comprises a hydrophobic material or a hydrophobic surface treatment, for example to reduce visible condensation of breath. In some embodiments the surface is textured for visual or aesthetic purposes.

The edge seal may be achieved with a soft, conforming, elastic or otherwise pliable material along the perimeter of the mask. The material may be configured to come into contact with the face and to at least partially conform to its contours. In some embodiments the edge material is a silicone rubber flap, cushion or gusset. Different types of silicone rubber with different mechanical properties can be used in the same mask, for example to provide more softness or pliability around the nose area where contours vary more significantly between different users. Other types of seal materials can be used including any suitable rubbers, foams or plastics. In some embodiments a natural or synthetic fiber-based material is used, such as fabric or paper. In other embodiments an air-filled cushion is configured along the edge of the mask, comprising a thin elastic material creating a tube or a cushion containing air.

FIGS. 9A-D show a number of non-limiting examples of mask aperture configurations. The breathing apertures in the shell can take any suitable form, including but not limited to a plurality of holes of any desired size or shape such as circular or polygonal holes; any other suitable form may be used. In some embodiments, such as FIG. 9B, the apertures can form an array of numerous small holes. In some embodiments the mask has multiple apertures of different shapes or dimensions. In other embodiments the apertures can be a plurality of elongated slits, including but not limited to a grille formed by parallel slits. Apertures can be located in the (hard) shell and in the (soft) cushion area. In other embodiments the apertures can be stylized geometrically for any functional or aesthetic purpose.

In some embodiments the apertures can have structure that provides some directionality or distribution to the air flow, such as relative to the mouth and nose or relative to the location of the sensing subassembly. This can be facilitated, for example, by tilted inner walls or protrusions, similar to an air distribution grille common in heating and air conditioning systems. In other applications the distribution of air flow inside the mask is affected by air channels, protrusions or wings inside the mask.

Figure 9A:
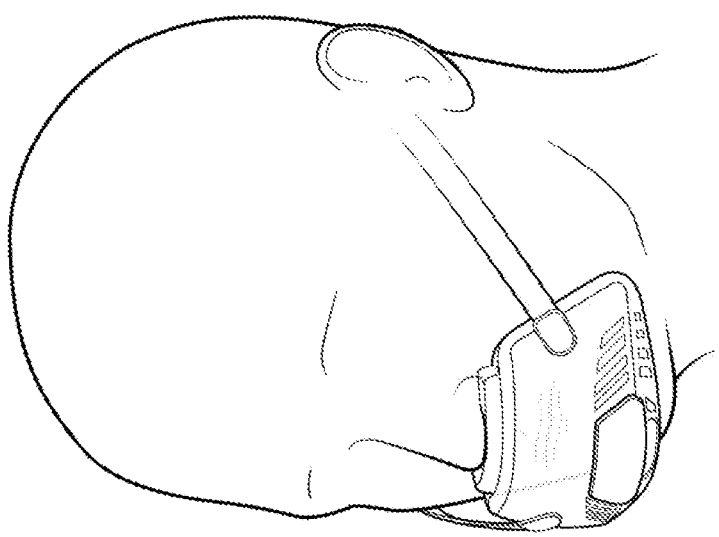
FIGS. 9A-D depict non-limiting examples of different mask and aperture configurations. It will be clear to a person skilled in the art that there are limitless other design choices possible, not only for the apertures but for the mask, the sensing module and the straps.
Figure 9B:
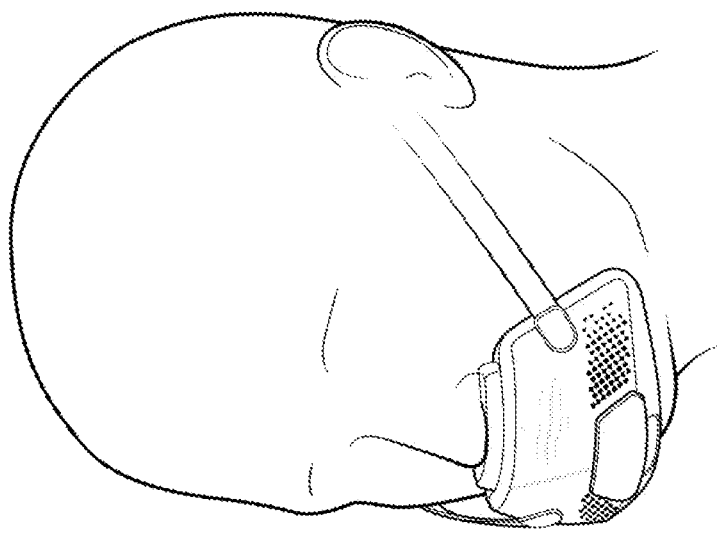
Figure 9C:
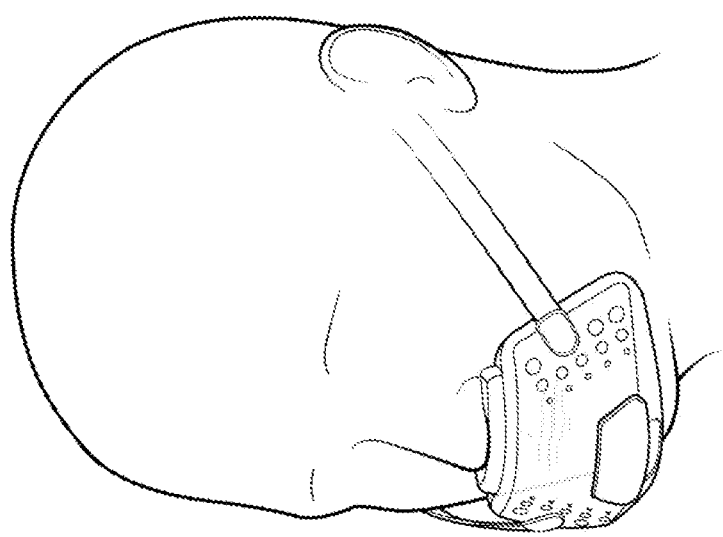
Figure 9D:
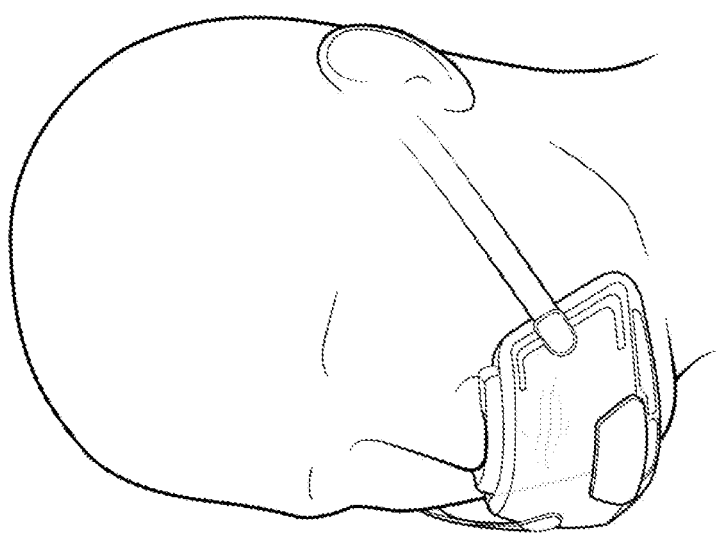

The relation between respiratory flow and DP readings can be influenced by the number and location of the apertures, as well as the flow patterns of air inside the mask. In some embodiments, multiple, smaller apertures are used, rather than a few large ones, to minimize sensitivity to variations in breathing patterns. A non-limiting example, for illustration purposes, is shown in FIG. 9B. In certain embodiments, aperture location is designed to eliminate or reduce direct exhalation from reaching at least some of the apertures directly in laminar flow. In a non-limiting example, apertures are located near the edges of the mask or at as much distance as practical from the mouth and nose. A non-limiting example is shown in FIG. 9D. In other embodiments, a mesh, filter or any other type of air permeable screen is configured over an aperture. In some embodiments, the mask further comprises a plurality of barriers or shields in the interior space, that can disrupt flow inside the mask, increasing turbulence or otherwise redistributing pressure and flow gradients more uniformly.

In some embodiments inhalation resistance may be reduced by incorporating one-way inhalation inlets. A non-limiting example is shown as (134) in FIG. 1A. In some embodiments, air flow is only determined during exhalation where the resistance generates higher (and therefore easier-to-measure) differential pressure. Conversely, other embodiments may provide lower exhalation resistance with one-way exhalation valves, and inhalation pressure may be relatively higher and easier to measure.

The mask can be attached to the face by any suitable apparatus. In some embodiments, one or more straps, laces or elastic bands behind the neck or the head hold the mask in place. In some embodiments, bands or straps behind the ears hold the mask in place. In some embodiments the mask is attached to a hat or head cover. In some embodiments the mask is attached to a harness around the head or the ears. In some embodiments the mask is "strapless," held in place by an adhesive material or adhesive layer between the skin and parts of the mask.

Communications & Applications. In some embodiments, the sensing module receives readings from the pressure sensor, the gas sensors, and any other sensors that may be included. The readings, or any calculated quantities derived from the readings (collectively, the "data") may be stored temporarily in electronic memory. In some embodiments, the module may transmit the data to one or more external receiving devices, which may receive the data and store it, analyze it, produce related reports and/or visual outputs, and/or share it with other devices. An external device can be a mobile computing device (e.g., a mobile phone, smartphone, tablet, gaming device, console, or wearable computing device), a stationary computer (e.g., a laptop computer, desktop computer, or server computer), and/or any other computing system, including a computing device which is embedded within a car or another system. Communication to an external device may be accomplished using any suitable communication protocol(s) and/or infrastructure, whether now known or later developed. For example, in some embodiments, such communication may be performed wirelessly, including but not limited to using Bluetooth®, BLE® LoRa®, and WiFi. For example, in some embodiments a Bluetooth® modem may be installed in the sensing module and transmit data to a nearby external device such as a smart phone or hand-held computer. In some embodiments, such communication may be wired. Any suitable way(s) of communicating data to one or more external devices may be employed.

In some embodiments the sensing module may accrue, compress and/or aggregate data before sending it to an external device. Accrued and/or aggregated data may, for example, be transmitted periodically (e.g., based on an amount of time having elapsed since a previous transmission) and/or based an amount of data having accrued. Additionally or alternatively, transmission of data may be initiated by a user or by an external receiving device.

Calorimetry and Biometrics. In some embodiments, sensor readings including (but not limited to) one or more of DP, oxygen concentration, $CO_2$ concentration, humidity, temperature, and barometric pressure, are used as inputs to calculate preliminary quantities including respiratory air flow (FF), oxygen consumption (VO2), and CO2 production (VCO2). In some embodiments, the preliminary quantities, along with certain sensor readings, can be used to convert or calculate "secondary" metrics, including but not limited to breath count (total breaths taken), breathing rate (breaths per minute, BPM), cumulative breathing volume (e.g., liters), respiratory exchange ratio (RER=VCO2/VO2) over any time interval, metabolic energy released (i.e., calories "burned"), and approximation of carbohydrates metabolized and fats or lipids metabolized (which can be expressed in grams or calories). In one example, carbohydrate metabolism is associate with an RER value of 1.0, whereas the average RER for typical lipids is approximately 0.7. In some embodiments a measured value of RER (between 0.7 and 1.0) can be used to impute a utilization ratio of these two classes of metabolic fuels, which is typically accurate as long as there is no significant energy metabolism using proteins. These and other biometrics can be calculated as instantaneous values and rates, or as cumulative or average values over a certain period.

The physiology underlying these biometrics is relatively well known to medical science, and some of the conversion formulas can be found in any number of texts (for example, "West's Respiratory Physiology" by J. B. West and A. M. Luks, $10^{th}$ ed., 2016; or "Energy Metabolism, Indirect calorimetry, and Nutrition" by S. Bursztein. 1989 Lippincott Williams & Wilkins). However, as noted above, the actual measurement of respiratory biometrics has thus far been restricted to laboratories, clinics or professional settings with complex, cumbersome and expensive equipment.

In some embodiments one or more calculations (e.g., relating to biometrics) may be performed "on-board" the sensing module itself. In some embodiments, one or more calculations may be performed by an external device, using data transmitted to a receiving device by the sensing module. In some embodiments, one or more calculations may be performed by a computing system that is not in direct communication with the sensing module (e.g., using data which is provided by one or more intermediate devices). Embodiments of the invention are not limited to being implemented in any particular way.

Generality. Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

Various aspects of the present invention may be used alone, in combination, or in a variety of arrangements not specifically discussed in the embodiments described in the foregoing, and it is, therefore, not limited in its application to the details and arrangement of components set forth in the foregoing description or illustrated in the drawings. For example, aspects described in one embodiment may be combined in any manner with aspects described in other embodiments.

The invention may be embodied as a method, of which various examples have been described. The acts performed as part of the method may be ordered in any suitable way. Accordingly, embodiments may be constructed in which acts are performed in an order different than illustrated, which may include different (e.g., more or less) acts than those which are described, and/or which may involve performing some acts simultaneously, even though the acts are shown as being performed sequentially in the embodiments specifically described above.

Use of ordinal terms such as "first," "second," "third," etc., to modify an element does not by itself connote any priority, precedence, or order of one claim element over another or the temporal order in which acts of a method are performed, but are used merely as labels to distinguish one element having a certain name from another element having the same name (but for use of the ordinal term) to distinguish the elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A system, configured to be worn on a user's head, for gathering respiratory air flow information about the user, the system comprising:

a mask, comprising a shell and a seal, the seal being arranged to contact a face of the user and to circumscribe an area of the face when the mask is worn by the user, the area of the face including a mouth of the user, the seal and the shell separating an interior space about the area of the face from an ambient space, the system being devoid of a tube for passing air exhaled by the user, the shell having a plurality of breathing apertures, each of the plurality of breathing apertures being configured to allow air from the ambient space to flow to the interior space, and to allow air exhaled by the user to flow from the interior space to the ambient space without passing through such a tube or through a conduit, thereby allowing the user to breathe while wearing the mask; and a sensing module, arranged for attachment to the mask, the sensing module comprising one or more air pressure sensors, one or more electronic components, and one or more batteries for powering the air pressure sensor(s) and the electronic component(s), the air pressure sensor(s) being configured to measure a pressure difference between the interior space and the ambient space, the electronic component(s) being configured to receive data from the air pressure sensor(s) and to enable determination of an air flow rate through the plurality of breathing apertures using the measured pressure difference, the electronic components(s) being further configured to transmit information to at least one external device, the information comprising the received data and/or a result of processing at least a portion of the received data.

2. The system of claim 1, comprising at least one selective flow element configured to limit the amount of air exhaled by the user that is allowed to proceed into the sensing zone module.

3. The system of claim 2, wherein the at least one selective flow element comprises an active seal or component, controlled by an electrical signal, configured to open selectively in response to exhalation so as to allow only exhaled air to flow into the sensing module.

4. The system of claim 2, wherein the at least one selective flow element comprises an aperture and a passive flap or cover on one side of the aperture, configured such that a positive pressure differential on one side pushes the flap open and enables air to flow through the aperture and a negative pressure differential on the other side seals the flap to a closed position and prevents air flow through the aperture.

5. The system of claim 1, wherein the area circumscribed by the seal and shell when the mask is worn by the user does not include a part of a bridge of the nose of the user.

6. The system of claim 1, wherein the shell is formed of a material which is at least partially transparent, so that the mouth of the user is at least partially visible through the shell when the mask is worn by the user.

7. The system of claim 1, wherein the shell comprises at least one breathing aperture with a one-directional flow element enabling air flow during inhalation, or during exhalation, but not both.

8. The system of claim 1, wherein at least one of the one or more air pressure sensors comprises a sensing port that extends to, or through, an aperture in the housing.

9. The system of claim 1, wherein the one or more electronic components are configured to wirelessly transmit the information to the at least one external device without the mask being physically connected to the at least one external device.

10. The system of claim 9, wherein the one or more electronic components are configured to enable determination of the air flow rate through the plurality of breathing apertures from the measured pressure difference (DP) between the interior and ambient spaces using conversion tables, formulas, coefficients, and/or parameters which are associated with properties of the mask or the plurality of breathing apertures.

11. The system of claim 9, wherein the one or more electronic components are configured to accrue information prior to transmission until such time that (i) the at least one external device is available and ready to receive the information, or (ii) the user initiates transmission via a program executing on the at least one external device.

12. The system of claim 9, wherein the one or more electronic components are configured to enable calculation of values regarding oxygen consumption by the user, CO2 production by the user, and/or at least one related or derived biometric or metabolic quantity.

13. The system of claim 12, where the at least one metabolic or biometric quantity includes any of (i) a respiratory exchange ratio, (ii) an amount of metabolic energy released or "calories burned", (iii) an amount or fraction of energy attributed separately to metabolizing different types of nutrients or physiological fuels, including but not limited to carbohydrates and fats.

14. The system of claim 9, wherein the one or more electronic components are configured to transmit the information to at least one external device with access to a global positioning system (GPS) or other geolocation data.

15. The system of claim 9, comprising the at least one external device.

16. The system of claim 1, wherein the sensing module comprises one or more gas sensors configured to measure a composition of air including but not limited to oxygen and carbon dioxide.

17. The system of claim 16, wherein the sensing module is configured with a flow path to receive exhaled air from the interior space directly, without said exhaled air flowing through the breathing apertures.

18. The system of claim 17, wherein the sensing module comprises a selective flow element configured to allow exhaled air to flow from the interior space to the air pressure and/or gas sensor(s) during exhalation and to prevent reverse air flow during inhalation.

19. The system of claim 1, wherein the mask is configured to make a seal around a base of a nose of the user.

* * * * *